United States Patent
Lungescu et al.

(10) Patent No.: US 12,159,261 B2
(45) Date of Patent: Dec. 3, 2024

(54) SYSTEM AND METHOD FOR SCREENING POTENTIAL TEST SUBJECTS FOR PARTICIPATION IN RECENT TRIALS

(71) Applicant: Independent Data Integrator, LLC, Fort Lauderdale, FL (US)

(72) Inventors: Alin Lungescu, Fort Lauderdale, FL (US); Darren Ellis Boyer, New York, NY (US)

(73) Assignee: Independent Data Integrator, LLC, Fort Lauderdale, FL (US)

( * ) Notice: Subject to any disclaimer, the term of this patent is extended or adjusted under 35 U.S.C. 154(b) by 13 days.

(21) Appl. No.: 18/155,724

(22) Filed: Jan. 17, 2023

(65) Prior Publication Data

US 2023/0177463 A1 Jun. 8, 2023

Related U.S. Application Data

(63) Continuation of application No. 16/995,782, filed on Aug. 17, 2020, now Pat. No. 11,556,893, which is a
(Continued)

(51) Int. Cl.
*G06Q 10/10* (2023.01)
*G06Q 30/018* (2023.01)
(Continued)

(52) U.S. Cl.
CPC .......... *G06Q 10/10* (2013.01); *G06Q 30/018* (2013.01); *G16H 10/20* (2018.01); *G16H 10/60* (2018.01)

(58) Field of Classification Search
CPC ........ G16H 10/00; G16H 10/20; G16H 10/40; G16H 15/00; G16H 20/00; G16H 20/10;
(Continued)

(56) References Cited

U.S. PATENT DOCUMENTS

| | | | |
|---|---|---|---|
| 2004/0073454 A1* | 4/2004 | Urquhart | G16H 10/60 705/2 |
| 2007/0239782 A1* | 10/2007 | Schneider | G06Q 10/10 |

OTHER PUBLICATIONS

Rajendram et al. 2008, "Protocol for the combined immunosuppression & radiotherapy in thyroid eye disease (CIRTED) trial: a multi-centre, double-masked, factorial randomised controlled trial," Trials. Jan. 31, 2008;9:6. doi: 10.1186/1745-6215-9-6. PMID: 18237441; PMCID: PMC2275219.*

(Continued)

*Primary Examiner* — Robert W Morgan
*Assistant Examiner* — Charles P Coleman
(74) *Attorney, Agent, or Firm* — Pearson IP; Loren Donald Pearson

(57) ABSTRACT

A system and method provide dosage information from past trials of potential subjects to clinics performing drug research so the clinics can determine if the potential subjects qualify (i.e., have waited sufficient time) to qualify for second trial. The system provides a clearinghouse that does not divulge the prior trials proprietary information to the requestor. Likewise, the system does not divulge to prior trial holders who is requesting subject information for subsequent trials. Biographical information including biometric identification can be used to identify subjects in the database. A further method allows a subject to confirm the data in the database.

5 Claims, 8 Drawing Sheets

Related U.S. Application Data continuation of application No. 12/689,964, filed on Jan. 19, 2010, now Pat. No. 10,783,598.

(60) Provisional application No. 61/145,384, filed on Jan. 16, 2009.

(51) Int. Cl.
*G16H 10/20* (2018.01)
*G16H 10/60* (2018.01)

(58) Field of Classification Search
CPC ........ G16H 20/13; G16H 20/17; G16H 30/00; G16H 40/00; G16H 50/00; G16H 70/00; G16H 10/60; G06Q 50/22–24; G06Q 10/10; G06Q 30/018
USPC .................................................. 705/3, 2, 20
See application file for complete search history.

(56) References Cited

OTHER PUBLICATIONS

Chow et al. 2008, "Adaptive design methods in clinical trials—a review," Orphanet J Rare Dis. May 2, 2008;3:11. doi: 10.1186/1750-1172-3-11. PMID: 18454853; PMCID: PMC2422839.*

* cited by examiner

SYSTEM AND METHOD FOR SCREENING POTENTIAL TEST SUBJECTS FOR PARTICIPATION IN RECENT TRIALS

CROSS-REFERENCE TO RELATED APPLICATIONS

This application is a continuation of prior application Ser. No. 16/995,782, filed Aug. 17, 2020, which is a continuation of prior application Ser. No. 12/689,964, filed Jan. 19, 2010, which claims the benefit of U.S. Provisional Application No. 61/145,384, filed Jan. 16, 2009. Each of the applications is hereby incorporated by reference.

STATEMENT REGARDING FEDERALLY SPONSORED RESEARCH OR DEVELOPMENT

Not Applicable

THE NAMES OF PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field of the Invention

The invention relates to clinical drug trials, and more particularly to screening potential subjects for participation in clinical drug trials.

Description of the Related Art

A need exists to screen potential drug-trial participants for participation in conflicting trials. In particular, there is a need for screening potential participants for sufficient "washing out periods".

Potential participants in drug trials may have incentive not to report their participation in other trials that may conflict with subsequent trials. Subjects who are ill and not treatable by available treatments may seek new treatments. Other potential participants enroll in drug studies for the money paid by the drug clinic. Participants seeking more or multiple payments may have an incentive to hide their participation in other trials so that they may enroll in multiple trials simultaneously or in more trials without completing the recommended wash-out period.

Some drug trials require a certain "wash out time" before the subject can participate in a subsequent trial. "Wash out time" may be the time required for a drug to fully elude from a subject's body. The wash out time may be the time for a prior drug's effects to end.

Under current investigations, medicine researchers (e.g. doctors, clinics, and other decision makers) lack complete prior drug dosing information about potential research participants. Research clinics invest time and money in screening potential participants to detect relevant blood levels and other inclusion/exclusion requirements dictated by clinical studies' protocols. In addition, clinics ask potential participants to make representations about the last time they received dosing of investigational medication. However, despite the current policies in place, there lies the potential that subjects may be enrolled in investigational medicine research studies without meeting proper "wash-out" criteria between dosing due to misrepresentations made by subjects about themselves.

This is a problem for two reasons. First, participants may be endangering their own health by enrolling in clinical studies without meeting the proper "wash-out" criteria. Secondly, the results of clinical studies may be compromised if the participating subjects have improper levels of foreign drug dosing in their bodies during the clinical research process.

BRIEF SUMMARY OF THE INVENTION

It is accordingly an object of the invention to provide a system for preventing subjects from participating in more than one research study at a time and to provide participating clinics with information needed to determine if a potential subject meets a trial's criteria of waiting between dosings of investigational medications.

The invention includes a system known as "Clinical RSVP". Clinical RSVP stands for Clinical Research Subject Verification Program. The system is an independent web-based clearinghouse that integrates a global central database and the individual identification mechanisms of biometrics and demographics to allow member clinics to access information regarding potential subjects. The system and method also provide a way for potential subjects to be screened without the prior clinic revealing to the subsequent clinic its prior study. Likewise, the system provides a way for the subsequent clinic to screen a subject without informing the prior clinic that it is performing a study. The system and method allow a clinic to view a potential subject's dosage history that is stored in a managed database.

Subjects participating in research studies are tracked in a central database. The central database includes the "dosing data" for individuals that have participated in research studies conducted at participating clinics. The dosing data can include the historical dosing dates. The dosing data can include the estimated final dosage date for a study. The dosing data is related to a subject identifier. A subject identifier is a unique identifier for each subject. Preferably, the subject identifier includes at least one immutable data relating to the subject. By including the immutable data, the subject is prevented from lying and creating a new subject identifier to avoid the screening. Examples of immutable data are biometric data, initials, date of birth, gender, and at least a portion of a social security number of the subject. Biometric data can be a fingerprint or retina scan.

Clinical RSVP is an independent clearinghouse where investigators (i.e. clinics) and other decision makers may submit and track information about potential and existing research participants that is useful for clinical study enrollment decisions. Clinical RSVP is a global application supported by a central database. The relevance of the information stored by Clinical RSVP is increased by the inclusiveness of its network, and the accuracy with which it is submitted.

The Clinical RSVP utilizes the following elements: Application Software, Logics, an Independent Central Database, Biometric Identification, Demographic Identifiers, Data Encryption, Data Security Processes, Subscribers/Users, Consent Form, and Participating Subject Discrepancy Mechanism.

Application Software. Clinical RSVP takes the form of an organized collection of computer data and instructions executed on a computer.

Logics. Clinical RSVP utilizes logical methodology such as restrictions, sequencing, reminders, alerts, and study closing procedures to produce reliable and relevant data while maintaining independence.

Independent Central Database. Subject identifier data is data used to determine dosing dates and wash-out time periods. The subject identifier data along with other data are stored at a central database. Once submitted, the data is housed independent of Clinical RSVP subscribers. This database serves as a central "clearinghouse" for registered clinics. Clinics will have access to limited data needed to make study enrollment decisions. This database can include any form of data collection stored under any form of support.

Biometric Identification. Clinical RSVP uses the measurement and recording of the physical characteristics of an individual for use in subsequent personal identification. Clinical RSVP utilizes biometric identification such as a fingerprint scanner to generate a map of an individual. This map is run against a global central database for participant identification purposes. The biometric is also used as a way for participants to verify the dosing dates entered into the database. Participants are instructed on how to provide their biometric in order to confirm that the dose dates are correct.

Demographic Identifiers. Clinical RSVP collects participant demographic identifiers such as initials, date of birth, sex, and last four digits of social security number to be used for participant identification purposes.

Data Encryption. The transfer of Clinical RSVP data occurs through encrypted connections. For example, data can be transferred in a TCP/IP Network via a connection supporting Hypertext Transfer Protocol Secure (HTTPS). A Virtual Private Network (VPN) can be used to connect each clinic to the Clinical RSVP.

Data Security Processes. Clinical RSVP requires effective data security measures. The data security process is summarized in the RSVP Data Security Policy.

Subscribers/Users. Access to Clinical RSVP data can be controlled user-by-user or by user type. For example, subscribers can be given access to Clinical RSVP data. These subscribers are the party responsible for entering the data, as well as the user of the data. Research clinic subscribers may directly or indirectly compete among each other for clinical studies. Therefore, the database is managed independently of the subscribers.

Consent Form. Clinical RSVP tracks information about individuals who have given signed consent to have their information included in the database.

Participating Subject Discrepancy Mechanism. Clinical RSVP utilizes an RSVP Accuracy Validation Form submitted by those individuals who have given signed consent to have their information included in the database to resolve potential participant discrepancies.

The system can provide a means to comply with laws protecting a subject's privacy. To comply with federal and state patient privacy laws, potential participants give their consent to be tracked by the RSVP application. Signed Subject consent forms are stored. The clinic itself might retain the consent. Alternatively, the signed consent forms can be stored electronically in the database. The RSVP consent form(s) are required to not violate HIPAA or any other regulatory statutes. If the provider prefers, the clinic can store the signed consent forms.

With the foregoing and other objects in view there is provided, in accordance with the invention, a system for confirming a subject's drug dosing history as it relates to that subject's ability to join a clinical drug study. The system includes an electronic database and a terminal connected to the database. The electronic database stores a subject identifier and the historical drug dosing information that is related to the subject identifier. The terminal accesses the database and is used for entering the subject identifier to be searched in the database in order to confirm the subject's drug dosing history to be used for making enrollment decisions about the next clinical study.

In accordance with the objects of the invention, a method for confirming a subject's ability to join a clinical drug study is also provided. The first step is checking if a subject identifier exists for a prior trial in the database. The next step is checking if the most-recent dosage date and/or estimated final dosage date do not conflict with the protocol of the proposed new trial.

For verification purposes, the clinic that enters data is related to each dosage record within the database with a unique clinic identifier. The clinic identifier is not published. Only, the database administrator can see which clinic entered a dosage record. If a potential subject challenges the correctness of a dosage record, the new clinic provides an accuracy validation form to the subject. The potential subject completes the accuracy validation form and submits the form to the database administrator. The database administrator then reviews the database, identifies the clinic that entered the data in question, contacts the clinic that entered the dosage information, and requests than an officer within the prior clinic verifies the data. The compliance officer then confirms the data and reports to the database administrator. The database administrator reports to the new clinic.

Each clinic does not know of the others request. The subsequent clinic cannot see the prior clinic's dosage data, so the identity and study information of the prior clinic is shielded from the subsequent clinic. Likewise, during a verification, the identity of the subsequent clinic is shielded from the prior clinic. The use of a middleman, the database administrator, allows the information to pass without passing information identifying each of the clinics.

Other features that are considered as characteristic for the invention are set forth in the appended claims.

Although the invention is illustrated and described herein as embodied in a clinical Research Subject verification program, it is nevertheless not intended to be limited to the details shown, because various modifications and structural changes may be made therein without departing from the spirit of the invention and within the scope and range of equivalents of the claims.

The construction and method of operation of the invention, however, together with additional objects and advantages thereof will be best understood from the following description of specific embodiments.

DETAILED DESCRIPTION OF THE INVENTION

Figure 8:
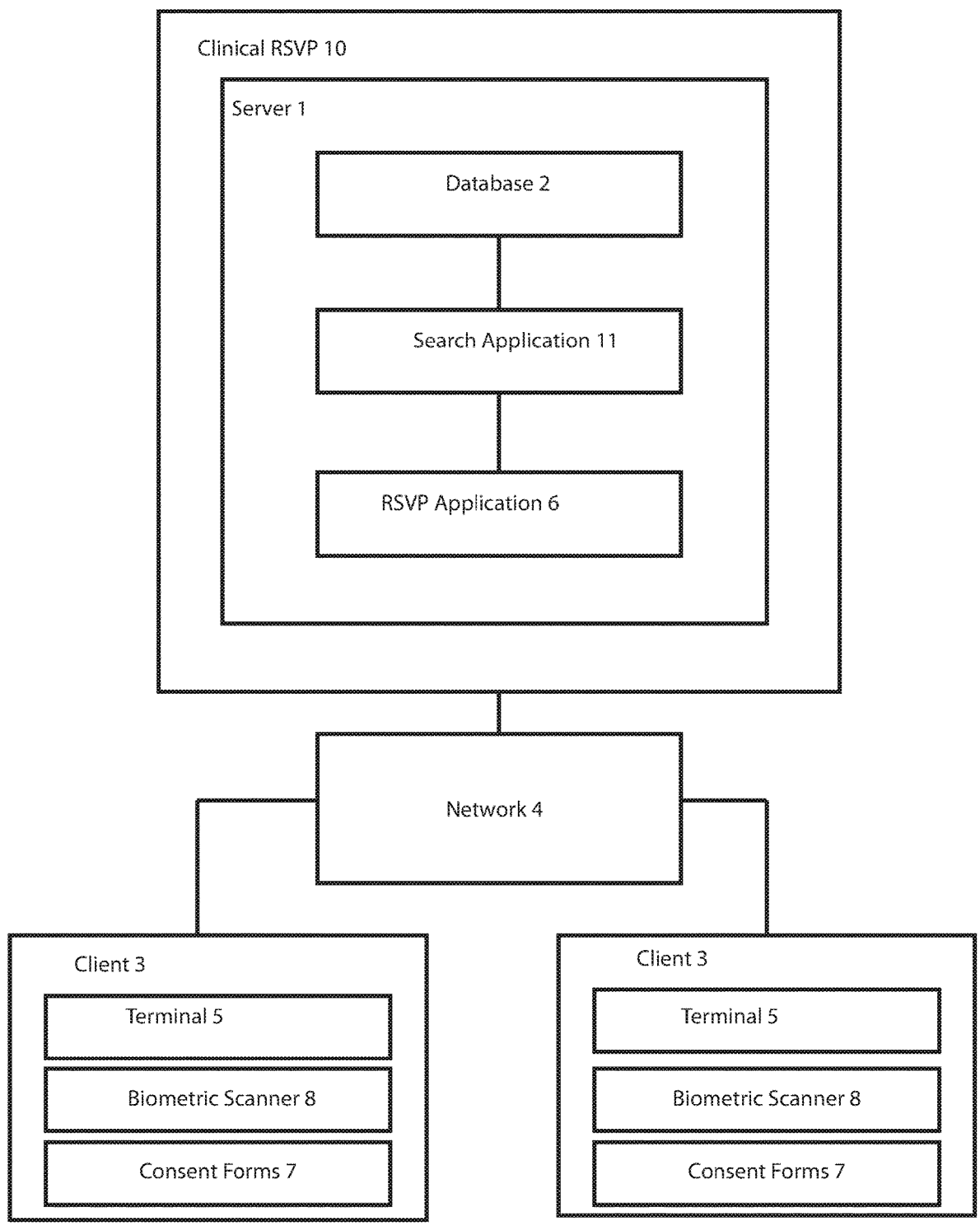
FIG. 8 is a schematic drawing of a system according to the invention.

FIG. 8 shows a preferred embodiment of a system according to the invention. The system which is referred to as "Clinical RSVP" includes a centralized computer database 2 hosted on a computer server 1. The computer server 1 is connected to clients via a network 4. Preferably, the network 4 is a TCP/IP network such as the Internet. Connections to the server 1 from the network 4 are secured with passwords, encryption, and other means for securing data communication over a network 4. Data being communicated across the network 4 is encrypted. A Virtual Private Network (VPN) is a preferred connection between the server 1 and the client 3.

Clinical research facilities are the preferred clients 3. Each clinical research facility 3 has a computer terminal 5, or more simply a "terminal", or workstation or other computer client for accessing the Clinical RSVP server 1 via the Internet 4. Each clinical research facility 3 is provided credentials (i.e. a username and password) to gain access to the Clinical RSVP server 1 and database 2.

Clinical research facilities 3 generate a unique study identification number in the database 2 by executing an RSVP application 6 on the server 1.

Clinical research facilities 3 have potential participants sign any and all consent forms 7 necessary to be tracked by Clinical RSVP 10.

Clinical research facilities 3 scan potential participant's fingerprint using a biometric fingerprint scanner 8. Based on the fingerprint scan, Clinical RSVP 10 then generates a unique biometric identifier number based on a template of the most determinant points of the fingerprint. The clinic 3 also collects the potential participant's initials, date of birth, sex, and last four digits of social security number to be used as additional participant identifier information.

Clinical research facilities 3 request that Clinical RSVP compare the identifier information obtained against the identifier information already stored in the central database 2.

Within the Clinical RSVP 10, a search application 11 on the server 1 searches the central database 2 for matches of identifier information, and reports the results of the search to the requesting clinic 3.

Clinical research facilities 3 submit data regarding study enrollment and dosing. Data is classified as Clinical Public Data, Clinical Proprietary Data, and Public Company Data.

Once data is submitted by research facilities, research participants provide their biometric identification to confirm the dosing information about themselves.

Clinical Public Data is defined as data that all subscribers to Clinical RSVP can access. The disclosure of this data is necessary for achieving the objective of Clinical RSVP. Clinic Public Data includes information that Clinical RSVP is obligated to protect. The value of Clinical RSVP would be destroyed or diminished if such information were disclosed outside the Clinical RSVP network. Some sensitive data necessary to achieve the objective of Clinical RSVP falls into this category. Examples of Clinical Public Data include Most Recent Reported Dose Taken Date, Scheduled Final Dose Date, Enrollment Status, unique biometric identifier number, participant initials, participant date of birth (D.O.B.), participant sex, and participant's last four digits of their social security number.

Clinical Proprietary data is any information that derives its economic value from not being disclosed across users or publicly disclosed. It includes information that Clinical RSVP is obligated to protect. The value of Clinical RSVP would be destroyed or diminished if such information were disclosed to others within the Clinical RSVP network or to others outside of the Clinical RSVP network. Examples of Clinical Proprietary Data include data audit trail, optional customized data fields, and unique study identification number.

Clinical Confidential Data is data not entered into Clinical RSVP but that is used to validate information entered into Clinical RSVP. Clinical confidential data is maintained by individual clinics that are subscribers to Clinical RSVP. This data is never to be communicated to the Clinical RSVP central database. However, for purposes of participant protection, subscribing clinics are required to reference this information to resolve discrepancy in the event that a participant submits an "Accuracy Validation Form". Clinical RSVP is not obligated to protect this data. Examples of Clinical Confidential Data include full participant name, participant medical information, clinical study name, clinical study enrollment reports, clinical study dosing dates, and clinical study key.

Public Company Data is defined as data that any entity, either internal or external to Clinical RSVP, can access. The disclosure, use, or destruction of Public Company Data will have limited or no adverse effects on Clinical RSVP nor carry any significant liability. Examples of Public Company Data include readily available news, public list of customers, and marketing information.

Figure 1:
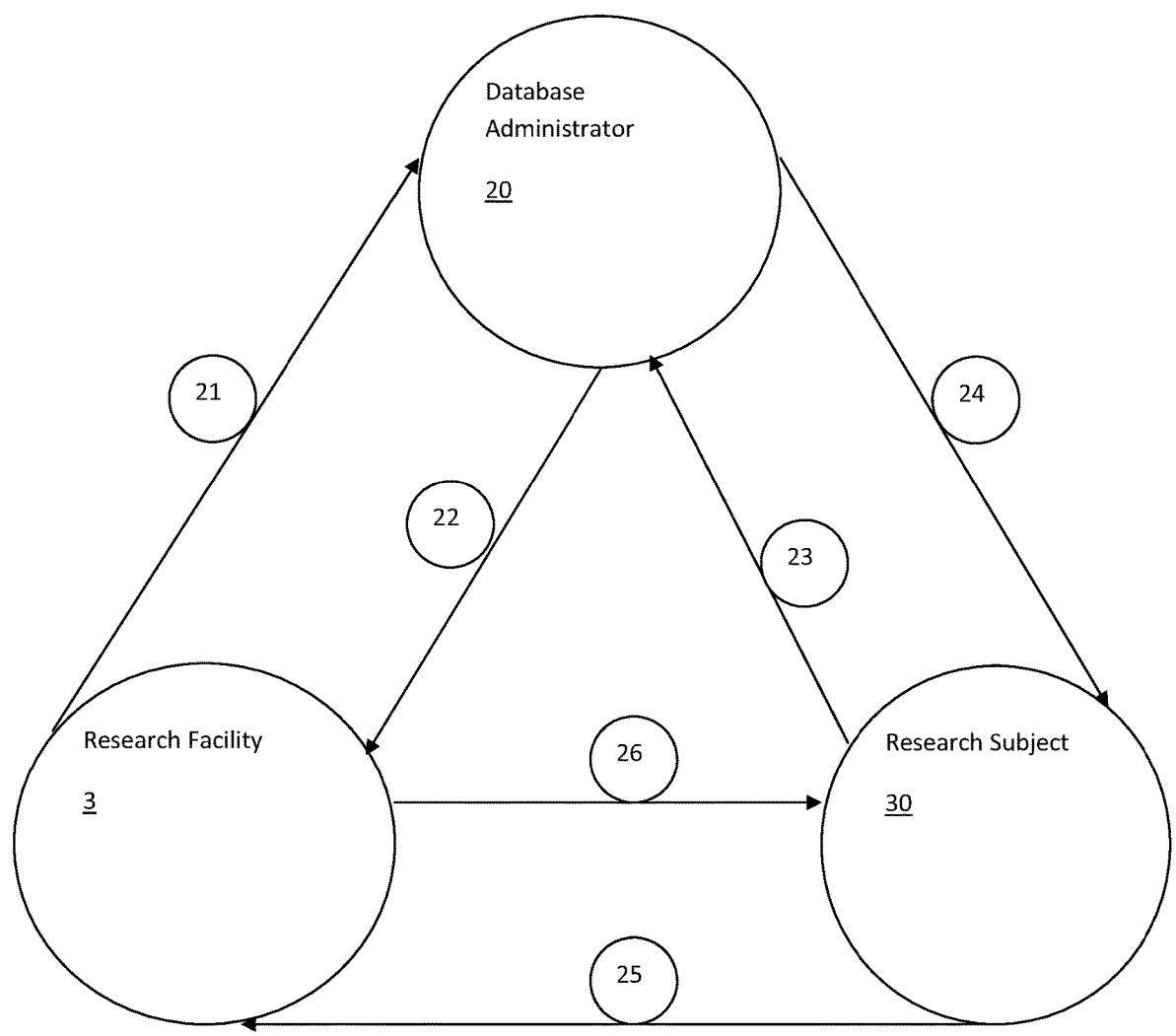
FIG. 1 is schematic diagram showing transfer of information within the system according to the invention.

FIG. 1 is a schematic drawing showing the relationship and transfer of information between database administrator 20, research facility 3, and research subject 30. A database administrator 20 manages the Clinical RSVP 10 and the database 2. A research facility 3 has a terminal 5 that is connected to the database 2. The research facility 3 enters data 21 including a subject identifier and dosage information into the database 2. Search results 22 of the database 2 are transmitted from the database 2 to the research facility 3. A subject 30 files an accuracy validation form 23 with the database administrator 20. The database administrator 20 transmits the results 24 of the verification to the research subject 30. The research facility 3 obtains the consent and subject identifier 25 information from the research subject 30. The research facility 3 provides the research subject with the accuracy validation form 26.

In the event a research subject files a RSVP Accuracy Validation form 23, the clinical research facility 3 is required to conduct an internal investigation, led by the facility's Accuracy Officer, as to the accuracy of any disputed dosing data.

Other products that could include our invention is any group of competitors that need to access shared marketplace data that is of the nature of being generated by the users which constitute the competing group, and of which is specific about individual persons. For example, competing clinics, doctors, or hospitals could include an embodiment of Clinical RSVP to track other relevant data about research participants or patients.

Modifications and substitutions that are merely design choices include the industry under which groups of competitors operate, the specifics of the data being tracked other than data about individual persons, and the permutations of the access to independently stored data.

The RSVP database program has adequate "encrypting" and data security protection processes.

Figure 2:
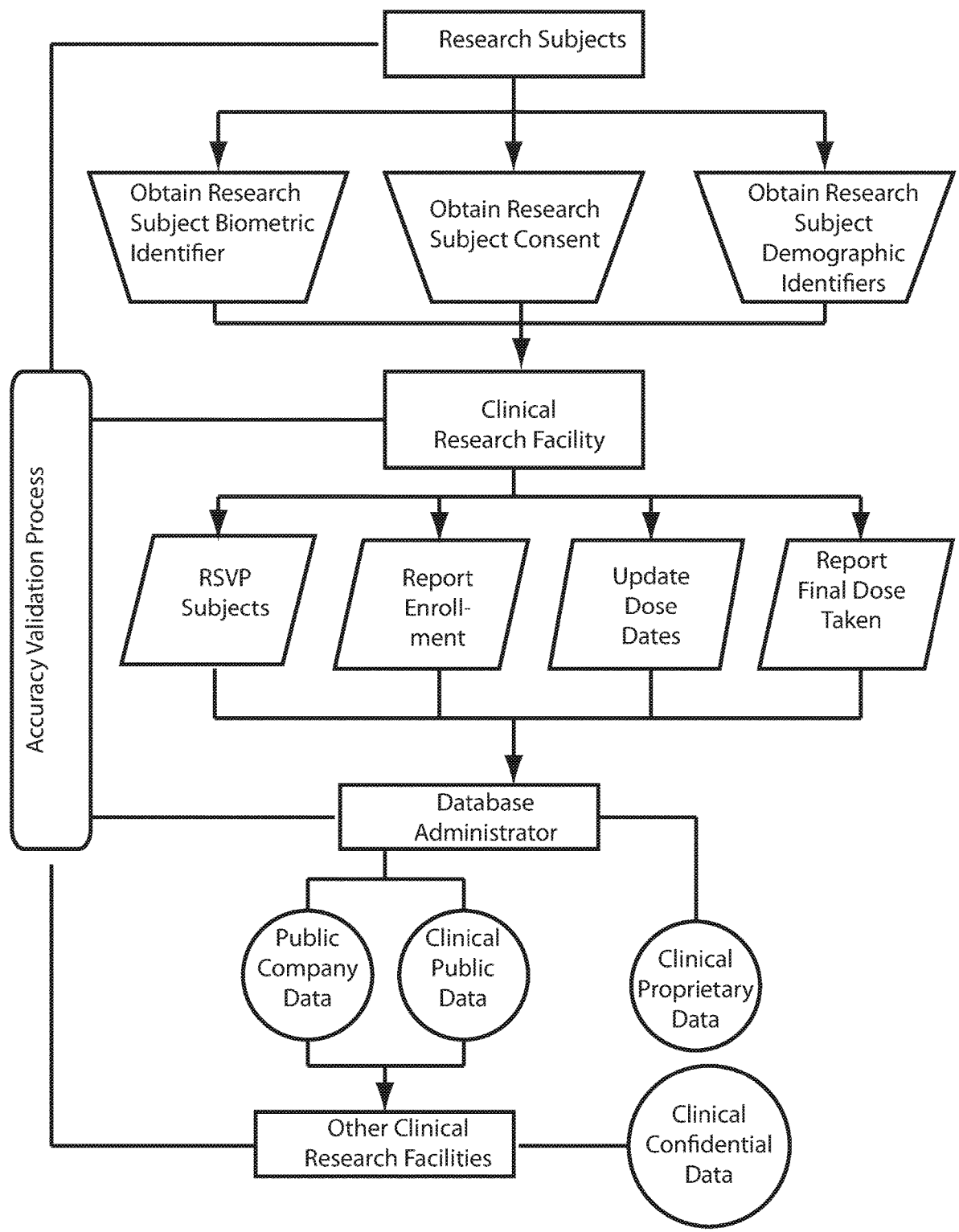
FIG. 2 is a flowchart showing a Clinical RSVP Configuration.

FIG. 2 is a flowchart showing a preferred embodiment of the system and method.

FIGS. 3-7 show related parts of the overall system and method.

Figure 3:
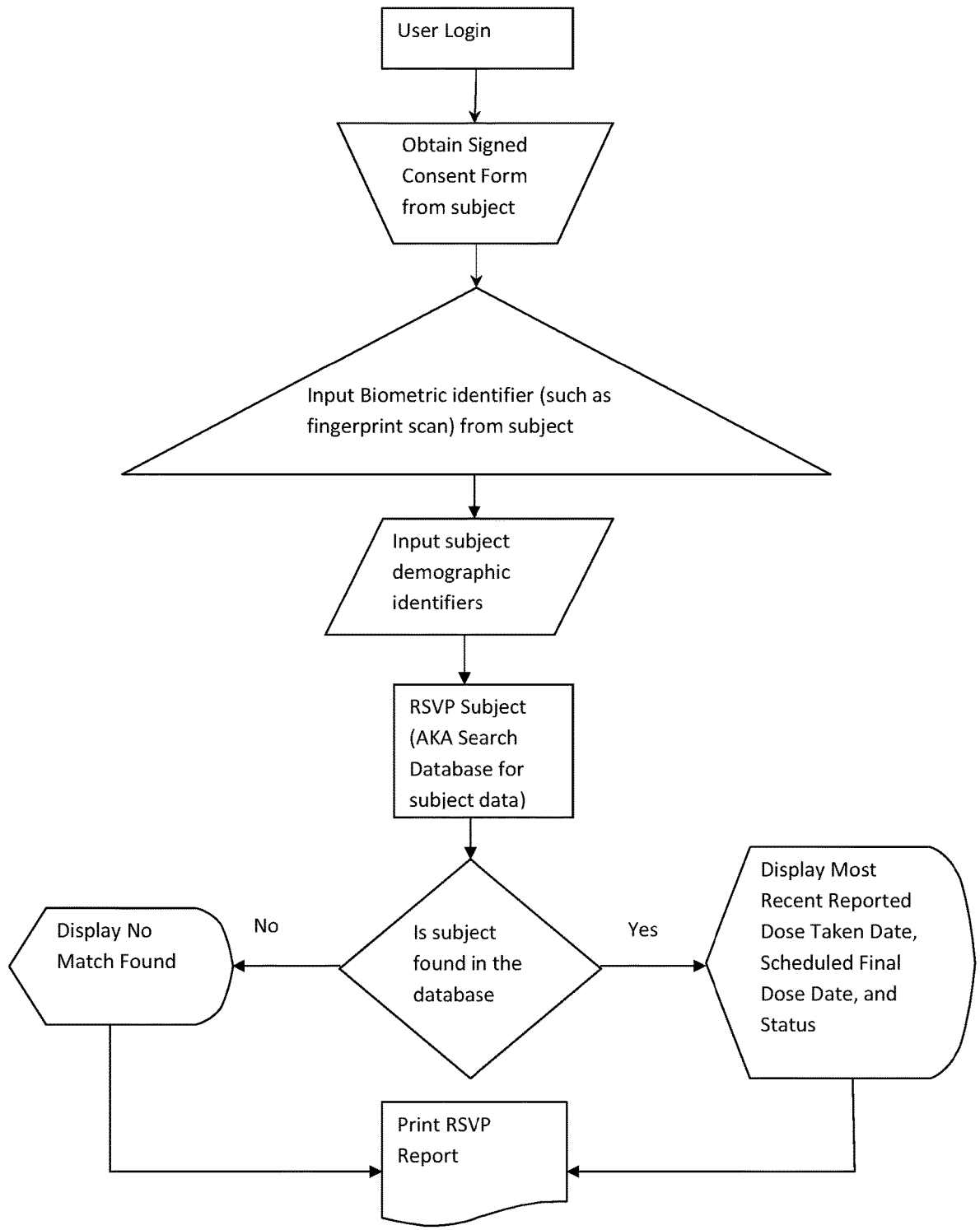
FIG. 3 is a flowchart showing a method for searching the database for a subject.

As shown in FIG. 3, at the time that a research subject 30 comes to the clinic 3 to screen for a research study, the clinic 3 logs to the Clinical RSVP system 10 via a terminal 5 through a website front end on the server 1. A clinic 3 is a center where subjects 30 may be screened, enrolled, and treated. The clinic 3 can be a research clinic or other place where healthcare is provided. The clinic 3 requests that the potential subject 30 sign a Personal Health Information Authorization Form: i.e. a consent form 7.

The clinic 3 will obtain subject identifiers. Preferably, the subject identifiers include an immutable biometric identifier such as a fingerprint or retina scan. A biometric scanner 8 is located at the clinic 3. The biometric scanner 8 is connected to the terminal 5. The clinic 3 uses the terminal 5 to transmit the biometric data to the Clinical RSVP. The clinic 3 also obtains biographical data from the subject 30. The biographical data is information used to identify the subject. Suitable biographical information includes an arbitrary alphanumeric identifier, initials, date of birth, gender, at least a portion of a social security number of the subject. Combinations of the data can be used to uniquely identify each subject 30 within the database 2.

If the subject 30 is new within the database 2, a record is created for the subject 30. As detailed below, if a record exists in the database for the subject 30, the dosage information for the subject 30 is output to the clinic 3.

The clinic 3 will then make an inquiry to the clinical RSVP database 2 to evaluate if a potential subject 30 has recently been dosed with an investigational medication. The clinic 3 utilizes a biometric identification hardware 8 to generate a unique biometric identifier number to identify the subject 30 and that unique identifier number will be searched in the database 2 to determine the most recent reported dose taken date, and scheduled final dose date (if any) of that potential subject 30. Also, the gender, date of birth, initials, and last four digits of the potential subject's social security number, will be obtained for searching the database 2.

Immediately prior to enrollment of a subject 30 into a research study, the clinic 3 will provide the RSVP application 10 with unique a unique subject identifier. The subject identifier preferably includes at least one immutable characteristic such as a biometric identifier number, the last four digits of the potential subject's social security number, gender, date of birth, and initials. The Clinical RSVP 10 will search for the subject identifier in the central database 2 and provide the clinic 3 with the date of inquired subject's last dose of study medication if a match is found. To protect the identity and subject matter of the prior clinical test, only the dosage information (i.e. most recent dosage and last planned dosage) of the subject 30 is preferably reported. Based on the most recent reported dose taken date and scheduled final dose date, the clinic 3 will decide if the subject 30 qualifies for the research study.

Figure 4:
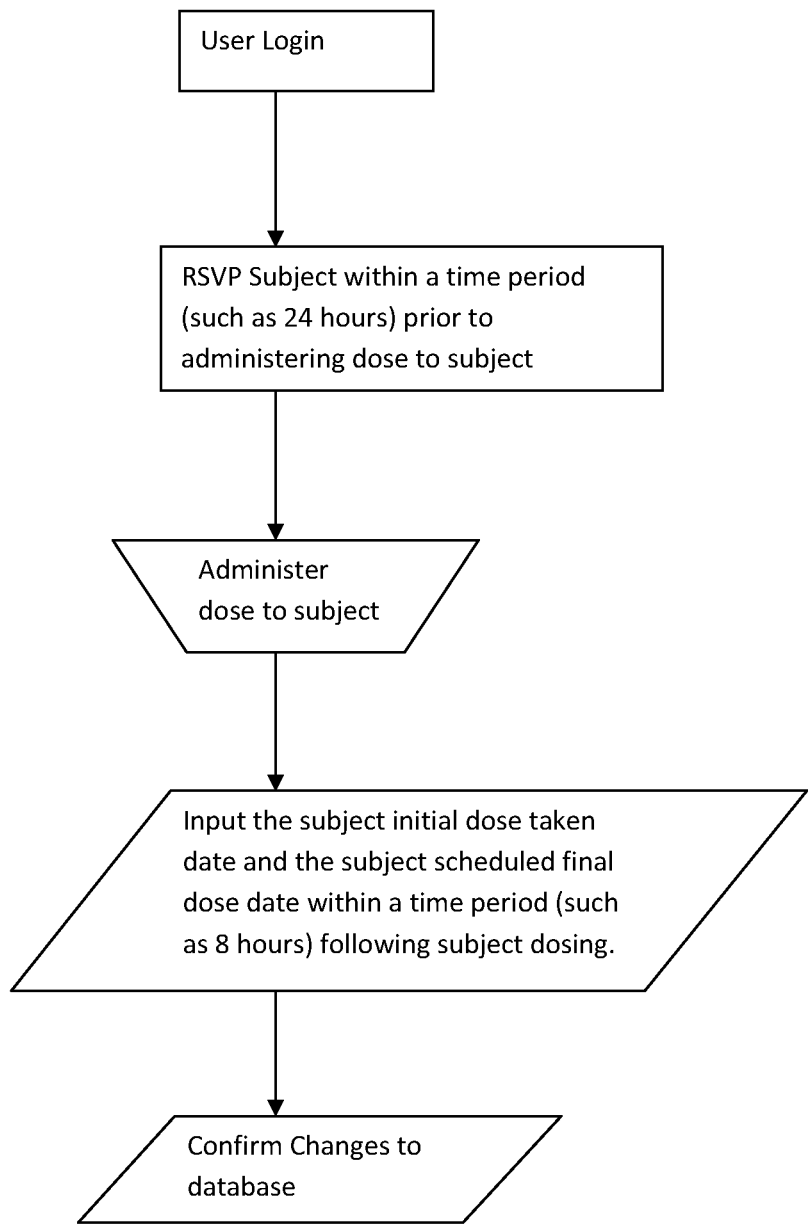
FIG. 4 is a flowchart showing a method for reporting enrollment of a subject.

As shown in FIG. 4, if a subject 30 is then enrolled in the research study, the clinic 3 will be required to update the database 2 (through the RSVP application) at, at least, initial dosing and final dosing to reflect the dosage information in the database 2. The clinic 3 confirms the dosage information before saving the dosage information in the database 2.

Figure 5:
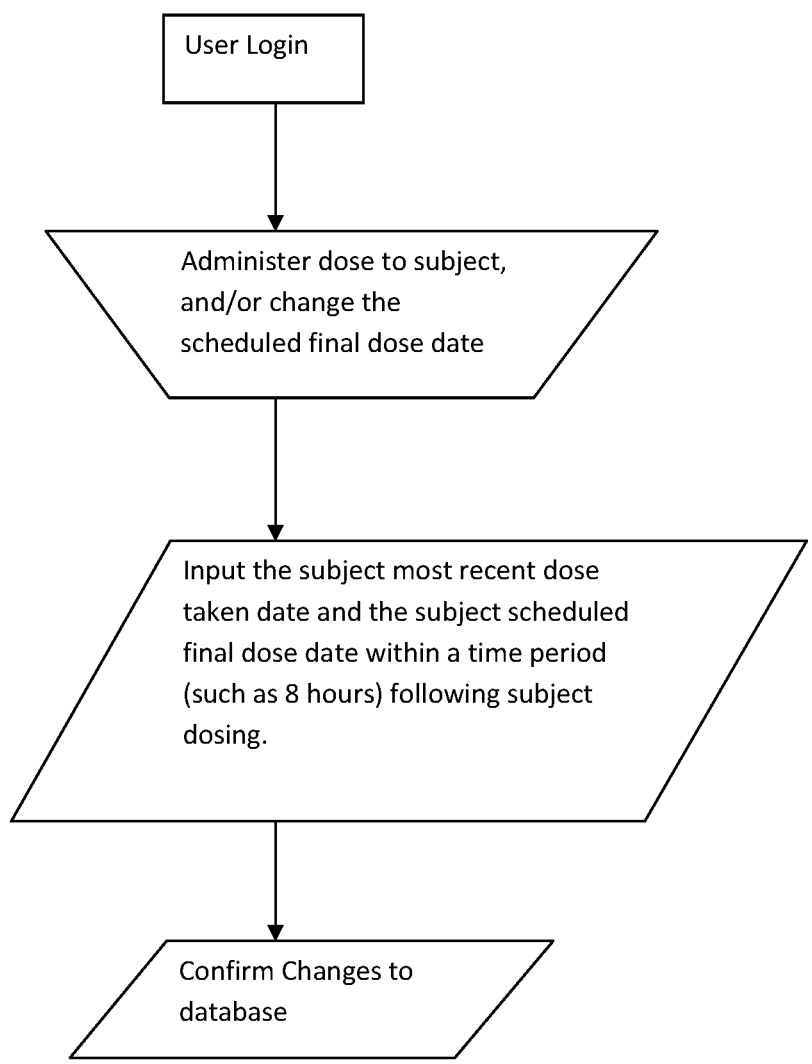
FIG. 5 is a flowchart showing a method for updating dose dates of a subject.

FIG. 5 shows the steps by which the dosage information is updated in the database 2. A user (i.e. a clinic 3) logs into the Clinical RSVP 10. The clinic 3 doses the subject 30. The clinic 3 records in the database 2 the dosage date and updates the anticipated final dosage date, if necessary. The clinic 3 uses the terminal 5 to enter into the database 2, the dosage information. The subject identifier, which preferably includes biometric data, is used to form a digital signature that is related to the dosing information being entered into the database 2. The clinic 3 confirms the change to the database 3 and the change is saved.

Figure 6:
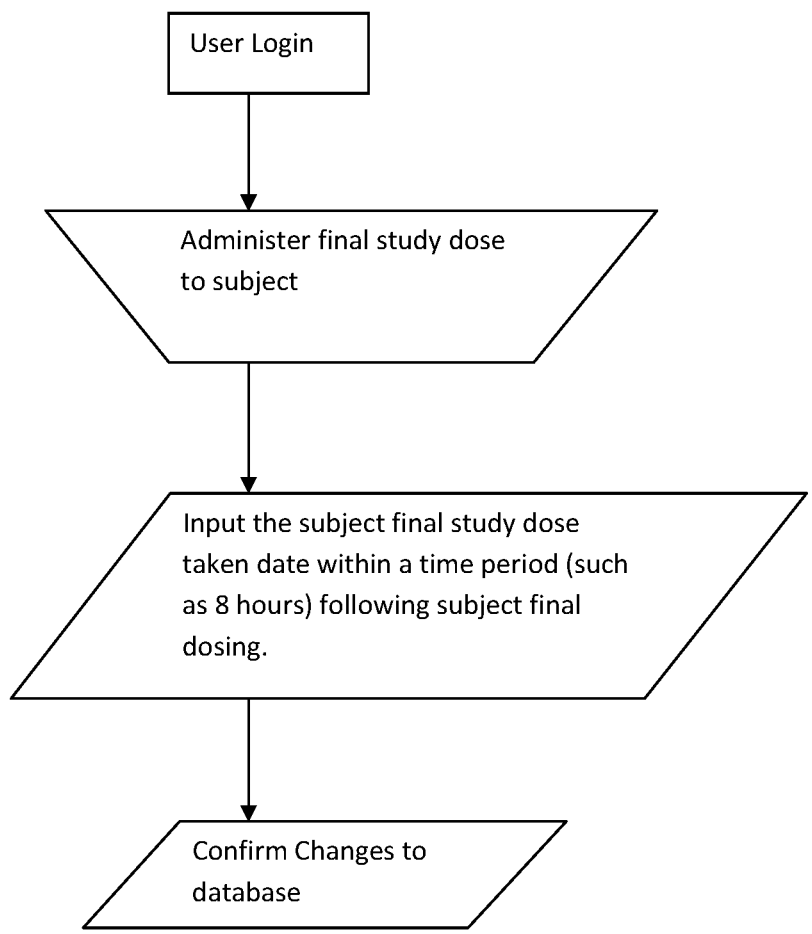
FIG. 6 is a flowchart showing a method for reporting a final dose taken.

FIG. 6 shows a flowchart illustrating a method for reporting a final dose taken by a subject. The clinic 3 begins by using the terminal 5 to login to the Clinical RSVP 10. A final dose is given to the subject 30. The clinic 3 updates the database 3 to show the final dose date. The clinic 3 confirms the change before the database 2 is updated.

Figure 7:
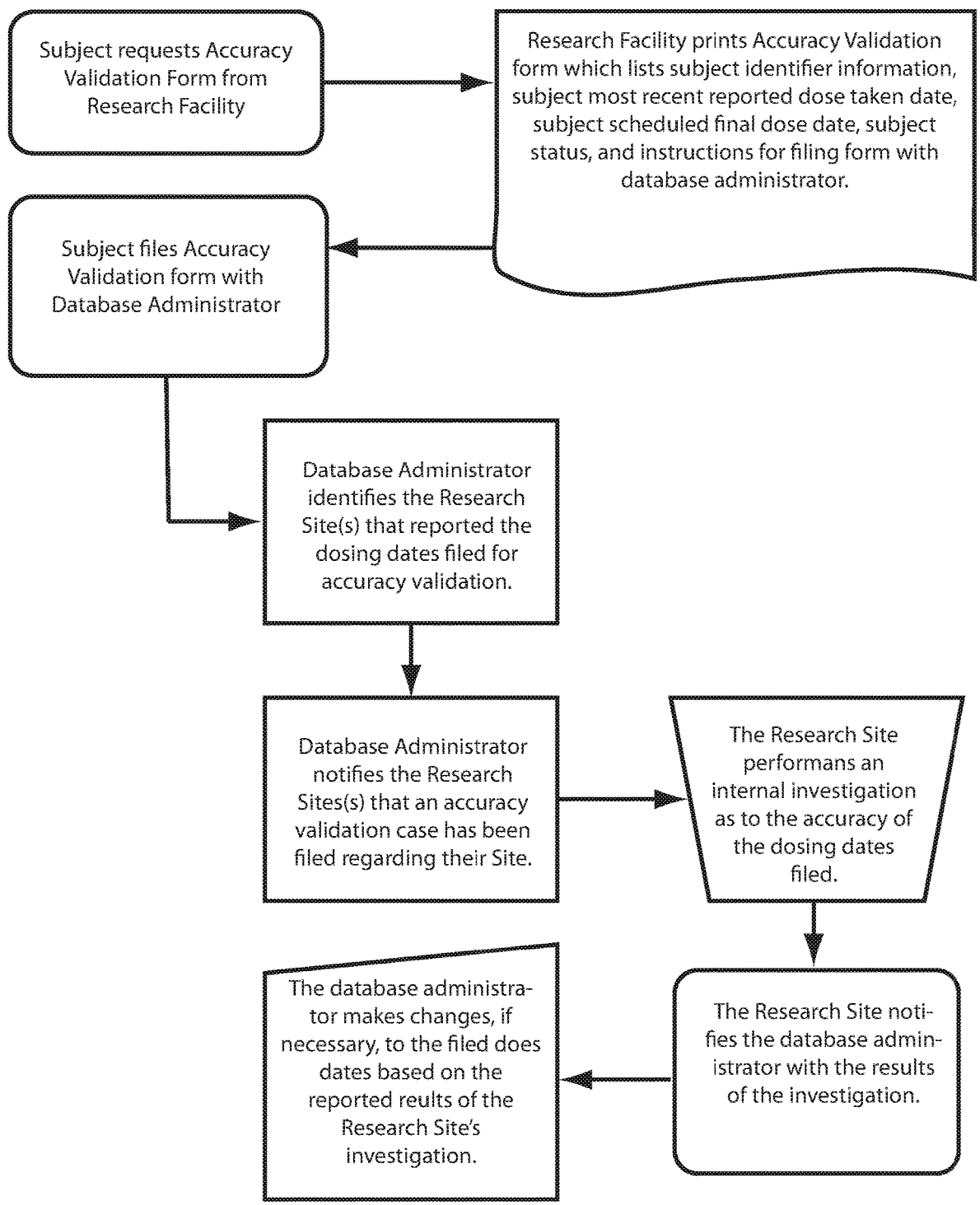
FIG. 7 is a flowchart showing a method for accuracy validating.

FIG. 7 is a flowchart depicting a preferred method for the accuracy of the database to be validated. Before data is validated, data is included in the database. An identifier associated with the study and the clinic 3 where the dosing occurs is generated and stored in the database 2 so as to be able to resolve any potential discrepancies (as claimed by subjects 30) that may occur. The clinic 3 and study identifier will not be released outside of the RSVP database and will be used only to resolve discrepancies.

Individual clinics will maintain all participant dosing history support documentation independent of the database administrator 20. Therefore, the database administrator 20 or other clinics 3 do not have access to information above and beyond the limited identifiers listed above. In the event of a subject discrepancy (i.e., the subject feels they are being unfairly withheld from the study due to inaccurate dosing date maintained in the system), the clinic 3 rejecting the subject 30 will provide the subject 30 with an RSVP Accuracy Validation form 23.

The RSVP Accuracy Validation Form 23 will list the following: date of report, all identifiers in the system, including the most recent reported dose taken date and scheduled final dosing date, phone number to the database administrator 20, and electronic submission option to the database administrator 20. In other words, in the event of a subject discrepancy, the subject 30 files an RSVP Accuracy Validation form 23 with the database administrator, who is independent from the clinic that inputted the data. Next, the database administrator searches the database 2 to find the subject identifier and the dosage information, which is being contested. Once obtained, the database administrator 20 sends the clinic 3 that made that data point entry a request. The clinic 3 then conducts an investigation, led by the clinic's self-appointed Accuracy Officer, as to the accuracy of the data under discrepancy. At least initially, the investigation confirms most recent reported dose taken date and schedule final dose date. The clinic 3 is then required to report the results of the investigation to the database administrator 20. The report confirms the subject's 30 most recent reported dose taken date and scheduled final dose date. If a mistake is found, the clinic sends corrected information to the Clinical RSVP 10. The new clinic 3 then may reevaluate the subject 30.

Accordingly, the preferred embodiment of the invention allows for a clinic to screen potential test subjects for recent participation in other studies that may compromise the results in the study or the health of the subject.

What is claimed is:

1. A computer implemented method for controlling administration of a medicinal dose to a candidate, the candidate possibly participating in a first clinical trial being held by a first clinic, the computer implemented method comprising:

treating a patient in the first clinical trial with a first medicinal dose at the first clinic on a first treatment date;
storing dosing information data in a first clinic database,
relating an identifier of the patient to the dosing information data in said first clinic database;
preventing a second clinic computer of a second clinic from accessing the first clinic database;
preventing a third clinic computer of the second clinic from accessing the first clinic database;
connecting an intermediary computer of an intermediary to a first clinic computer via a network;
reading the first clinic database with said intermediary computer via the network;
storing an identifier of the first clinic in an intermediary database hosted in said intermediary computer;
storing an identifier of the candidate in a second clinic database, said second clinic database being hosted in said second clinic computer, said second clinic database being computerized;
connecting said intermediary computer to said second clinic computer via a computer network;
storing an identifier of the candidate in a third clinic database, said third clinic database being hosted in said third clinic computer, said third clinic database being computerized;
connecting said intermediary computer to said third clinic computer via a computer network;
sending a request from the second clinic computer to the intermediary computer, the request including an identifier of the second clinic and the identifier of the candidate;
storing the request in the intermediary database;
generating a query from the request by removing the identifier of the second clinic from the request and adding a query identifier to the query, the query identifier being assigned by said intermediary;
storing the query identifier in the intermediary database;
relating the query identifier to the request in the intermediary database;
sending the query from the intermediary computer to the first clinic computer via the network;
sending the query from the intermediary computer to the third clinic computer via the network;
generating with said first clinic computer a query result from the first clinic database when the identifier of the candidate matches the identifier of the patient, the query result including the dosing information data, said identifier of said first clinic, and the query identifier;
transmitting the query result from the first clinic computer to the intermediary computer;
storing the query result in the intermediary database;
generating a response from the query result by removing the identifier of the first clinic from the query result;
generating with said third clinic computer a second query result, said second query result being generated from the third clinic database, when the identifier of the candidate matches the identifier of the patient, the second query result including the dosing information data, said identifier of a third clinic, and the query identifier;
transmitting the second query result from the third clinic computer to the intermediary computer;
storing the second query result in the intermediary database;
generating a response from the query result by removing the identifier of the third clinic from the query result;
comparing the query result from the first clinic and the second query result from the third clinic to create machine learning algorithms;
comparing the query result from the first clinic and the second query result from the third clinic to perform predictive modelling;
comparing the query result from the first clinic and the second query result from the third clinic to develop artificial intelligence;
comparing the query result from the first clinic and the second query result from the third clinic to perform cohort analysis, enrollment feasibility analysis, enrollment simulations, optimal candidate identification, patient-trial matching, and streamlined recruitment workflows:
transmitting the response from the intermediary computer to the second clinic computer via the network; and
based on the response from the intermediary computer, treating the candidate with said medicinal dose in a second clinical trial at the second clinic under a condition that the query result, the second query result, and any analysis of both said query results does not conflict with a protocol of the second clinical trial.

2. The computer implemented method according to claim 1, wherein said dosing information data includes patient clinical records for clinical trial qualification information.

3. A system for controlling administration of a medicinal dose to a candidate, the candidate possibly participating in a first clinical trial being held by a first clinic, the system comprising:

an intermediary computer hosting an intermediary database;
said intermediary computer receiving a second-clinic query from a second clinic, the second-clinic query including a candidate identifier of the candidate and a second-clinic identifier, the candidate identifier identifying the candidate, the second-clinic identifier identifying the second clinic;
said intermediary computer storing the second-clinic query in said intermediary database;
said intermediary computer generating a first-clinic query from the second-clinic query by including the candidate identifier and removing the second-clinic identifier;
said intermediary computer relating the first-clinic query to the second-clinic identifier in said intermediary database;
said intermediary computer transmitting the first-clinic query to a first clinic;
said intermediary computer receiving a first-clinic query result from the first clinic, the first-clinic query result including a first-clinic identifier and dosage information of the candidate, the first-clinic identifier identifying the first clinic;
said intermediary computer relating the first-clinic query result to said first-clinic query in said intermediary database;
said intermediary computer generating a second-clinic query result from the first-clinic query result by including the dosage information of the candidate and by removing the first-clinic identifier; and said intermediary computer transmitting the second-clinic query result to the second clinic.

4. A computer implemented method for controlling administration of a medicinal dose to a candidate, the candidate possibly participating in a first clinical trial being held by a first clinic, the computer implemented method comprising:
- hosting an intermediary database;
- receiving a second-clinic query from a second clinic, the second-clinic query including a candidate identifier and a second-clinic identifier, the candidate identifier identifying the candidate, the second-clinic identifier identifying the second clinic;
- storing the second-clinic query in said intermediary database;
- generating a first-clinic query from the second-clinic query by including the candidate identifier and removing the second-clinic identifier;
- relating the first-clinic query to the second-clinic identifier in said intermediary database;
- transmitting the first-clinic query to a first clinic;
- receiving a first-clinic query result from the first clinic, the first-clinic query result including a first-clinic identifier and dosage information of the candidate, the first-clinic identifier identifying the first clinic;
- relating the first-clinic query result to said first-clinic query in said intermediary database;
- generating a second-clinic query result from the first-clinic query result by including the dosage information of the candidate and by removing the first-clinic identifier; and
- transmitting the second-clinic query result to the second clinic.

5. The computer implemented method according to claim 4, further comprising disqualifying the candidate at the second clinic based on the dosing information in the second-clinic query result.

* * * * *